US00PP10346P

United States Patent [19]

van Andel

[11] Patent Number: Plant 10,346

[45] Date of Patent: Apr. 21, 1998

[54] ALSTROEMERIA PLANT VARIETY NAMED 'STAPRIZSA'

[75] Inventor: Jacob van Andel, Aalsmeer, Netherlands

[73] Assignee: Van Staaveren B.V., Aalsmeer, Netherlands

[21] Appl. No.: 716,484

[22] Filed: Sep. 16, 1996

[51] Int. Cl.[6] ..... A01M 5/00

[52] U.S. Cl. ..... Plt./87.1

[58] Field of Search ..... Plt./87.1

[56] References Cited

U.S. PATENT DOCUMENTS

P.P. 6,036 10/1987 Van Andel ..... Plt./87.1

*Primary Examiner*—James R. Feyrer
*Assistant Examiner*—Kent L. Bell
*Attorney, Agent, or Firm*—Christie, Parker & Hale, LLP

[57] ABSTRACT

A new and distinct Alstroemeria plant variety producing flowers of good quality and attractive coloration, suitable for growing in pots.

1 Drawing Sheet

BACKGROUND OF THE INVENTION

The present invention relates to a new and distinct variety of Alstroemeria hybrid originated as a seedling by crossing as seed parent an unreleased, unpatented seedling identified as 91D196-1 and as pollen parent an unreleased, unpatented seedling identified as 7G1069-02 from among my collection of Alstroemeria seedlings maintained under controlled conditions in a greenhouse at Van Staaveren B.V., Aalsmeer, The Netherlands, for developmental purposes. The varietal denomination of the new variety is 'Staprizsa'.

The first act of asexual reproduction of 'Staprizsa' was in Aalsmeer, The Netherlands, by propagation by dividing rootstocks. Asexual reproduction in Aalsmeer, The Netherlands, through successive generations has demonstrated that the combination of characteristics as herein disclosed for 'Staprizsa' are firmly fixed and retained through successive generations of asexual reproduction.

'Staprizsa' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Staprizsa' are characterized by flowers of unusual coloration, as described herein. The new variety is especially suitable for growing in pots.

DESCRIPTION OF ILLUSTRATIONS

The new variety of Alstroemeria hybrid is illustrated in the accompanying illustration, which shows typical growth and flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
*Family.*—Amaryllidaceae.

*Genus.*—Alstroemeria sp.
*Commercial.*—Alstroemeria hybrid.
Origin: Seedling.

Plant

Form: Bush, pot-type.
Shape: Upright.
Height: About 25 to 40 cm.
Main stem or cane length: About 30 cm.
Growth: Vigorous, medium growth rate.
Strength: Strong.
Foliage:
*Quantity.*—Abundant.
*Number of leaves.*—About 20 to 25.
*Size of leaf.*—Length: About 3 to 10 cm. Width: About 1 to 2 cm.
*Shape of leaf.*—Elliptical.
*Margin type.*—Minutely crimped.
*Texture.*—Smooth.
*Color.*—Upper side: Near 143A. Underside: Near 143B.
*Rhizomes.*—Yes. Color: Near 155D. Size: About 10–15 cm.

Inflorescence — Flower/Floret

Blooming habit: Intermittent.
Blooms: Profusely.
*Spring.*—Yes.
*Fall.*—Yes.
*Has tendency to give few blooms in fall.*—No.
Size: Medium.
*Diameter.*—About 5–6 cm.
*Depth.*—About 4–5 cm.
Borne: Singly along simple racemes.
Shape or form:
*When bloom first opens.*—Cup.
*When bloom matures.*—Cup.
Petalage:
*Number of petals.*—6.
*Arrangement.*—Two concentric circles of 3 petals.
*Form.*—Obovate.
*Margin type.*—Straight.
*Apex.*—Pointed.
*How long do petals stay on stem?*—About 3 weeks.
*Texture.*—Leathery.
*Appearance.*—Shiny.

*Color.*—Outer petal: Body near 52B; base near 52B; reverse side near 52C; no stripes. Inside petal: Body near 52B to 12A; base near 52B; reverse side near 52C to near 12A; about 20 to 30 stripes, near 185A.

Peduncle or flower stem:
*Length.*—About 2 to 3 cm.
*Color.*—Near 143A.
*Strength.*—Strong.
*Upright.*—Yes.

Discoloration after full bloom? Slightly, from near 52B to near 52C.

Is bloom affected by wet or hot weather? No.

Persistence (does flower hang on and dry?): No.

Disease resistance: Unknown. p0 Fragrance: None.

Lasting quality:
*On plant.*—About 3 weeks.
*As cut flower.*—About 14 days.

Bud

Size:
*Diameter.*—About 1 cm.
*Depth or length.*—About 2 cm.

Form or shape: Pear-shaped.
*Long.*—Yes.
*Pointed.*—No, ovoid.

Rate of opening: Fast.

Color of petals:
*When petals begin to unfurl.*—Near 52B.

Peduncle or flower stem:
*Length.*—About 2 to 3 cm.
*Hairy.*—No.
*Strength or character.*—Erect.
*Color.*—Near 143A.

Reproductive Organs

Stamen:
*Number.*—6.
*Arrangement.*—Around the style.

Anthers:
*Size.*—About 8 to 10 mm.
*Color.*—Near 152C.

Filaments:
*Length.*—About 5 cm.
*Color.*—Near 65C.

Pollen:
*Color.*—Near 152A.

Pistils:
*Number.*—1.

Styles:
*Length.*—About 4 to 5 cm.
*Color.*—Near 65C.

Stigmas:
*Color.*—Near 52B.

Fruit

Fertile: Yes.

Shape: Round.

Color at maturity: Near 164A.

I claim:

1. A new variety of Alstroemeria plant substantially as herein shown and described, suitable for growing in pots.

* * * * *

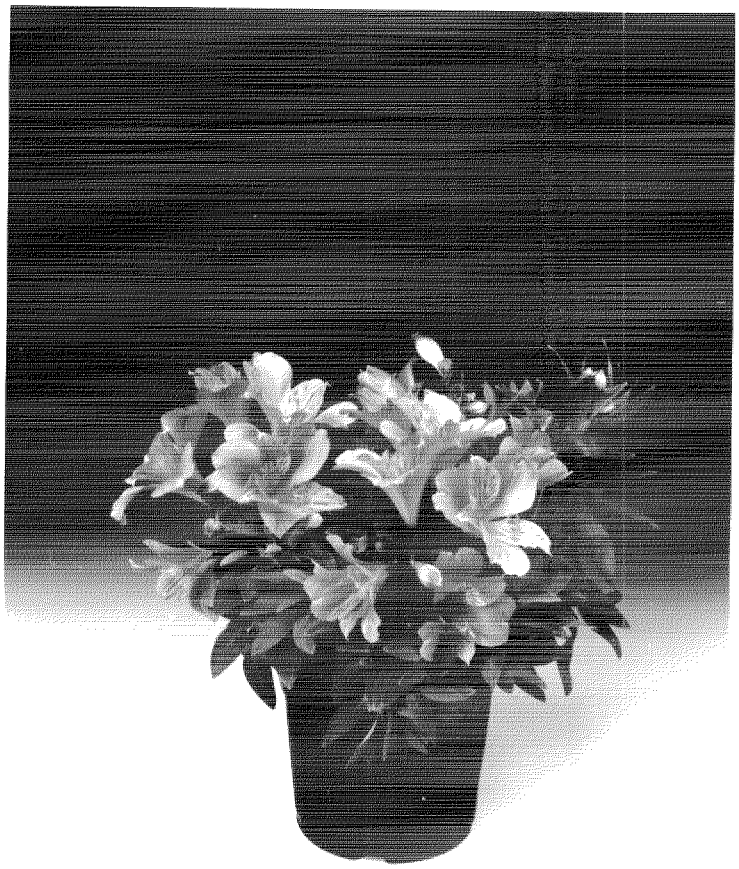

UNITED STATES PATENT AND TRADEMARK OFFICE

CERTIFICATE OF CORRECTION

PATENT NO. : Plant 10,346
DATED : April 21, 1998
INVENTOR(S) : Jacob van Andel

It is certified that error appears in the above-indentified patent and that said Letters Patent is hereby corrected as shown below:

Column 3, line 14, replace
"Disease resistance: Unknown. P0 Fragrance: None." with
-- Disease resistance: Unknown. Fragrance: None. --.

Column 4, line 24, between "Fertile: Yes." and "Shape: Round" insert
-- Size: About 3 to 10 cm in length, and about
1 to 2 cm in width.
Texture: Smooth.
Margin: Straight.
Color: Topside near 143A, underside near 143B. --.

Signed and Sealed this

Twenty-fourth Day of November, 1998

*Attest:*

*Attesting Officer*

BRUCE LEHMAN

*Commissioner of Patents and Trademarks*